(12) United States Patent
Hsien

(10) Patent No.: US 7,013,737 B2
(45) Date of Patent: Mar. 21, 2006

(54) REMOVABLE TWISTING MEASURING DEVICE FOR VARIOUS HAND TOOLS

(76) Inventor: Chin-Ching Hsien, 235 Chung - Ho Box 8-24, Taipei (TW)

( * ) Notice: Subject to any disclaimer, the term of this patent is extended or adjusted under 35 U.S.C. 154(b) by 129 days.

(21) Appl. No.: 10/782,907

(22) Filed: Feb. 23, 2004

(65) Prior Publication Data

US 2005/0183513 A1 Aug. 25, 2005

(51) Int. Cl.
*G01N 3/24* (2006.01)
(52) U.S. Cl. ...................... 73/841; 73/862.21
(58) Field of Classification Search .................. 73/841, 73/862.21, 862.22, 862.24, 862.25, 862.26
See application file for complete search history.

(56) References Cited

U.S. PATENT DOCUMENTS 5,303,601 A * 4/1994 Schonberger et al. .... 73/862.23
6,766,700 B1 * 7/2004 Hsien ...................... 73/862.21
6,784,799 B1 * 8/2004 Hsien .......................... 340/668

* cited by examiner

*Primary Examiner*—Edward Lefkowitz
*Assistant Examiner*—Linda P. Field

(57) ABSTRACT

A removable twisting measuring device for various hand tools comprises a cover removably installed on a rod body of a hand tool; a strain gauge installed at one end of the cover contacting the rod body of the hand tool; the strain gauge having a deformation due to a twisting force; a display device having a transfer element; resistance variation due to the deformation of the strain gauge being transferred to the display device so as to derive the twisting force which is then displayed on the display device. The display device can be installed to another removable covers. Moreover, outlooks of the covers are matched to the hand tool. The cover is made from one of aluminum alloys and deformable materials. The display device has a screen and a calibrating button.

3 Claims, 10 Drawing Sheets

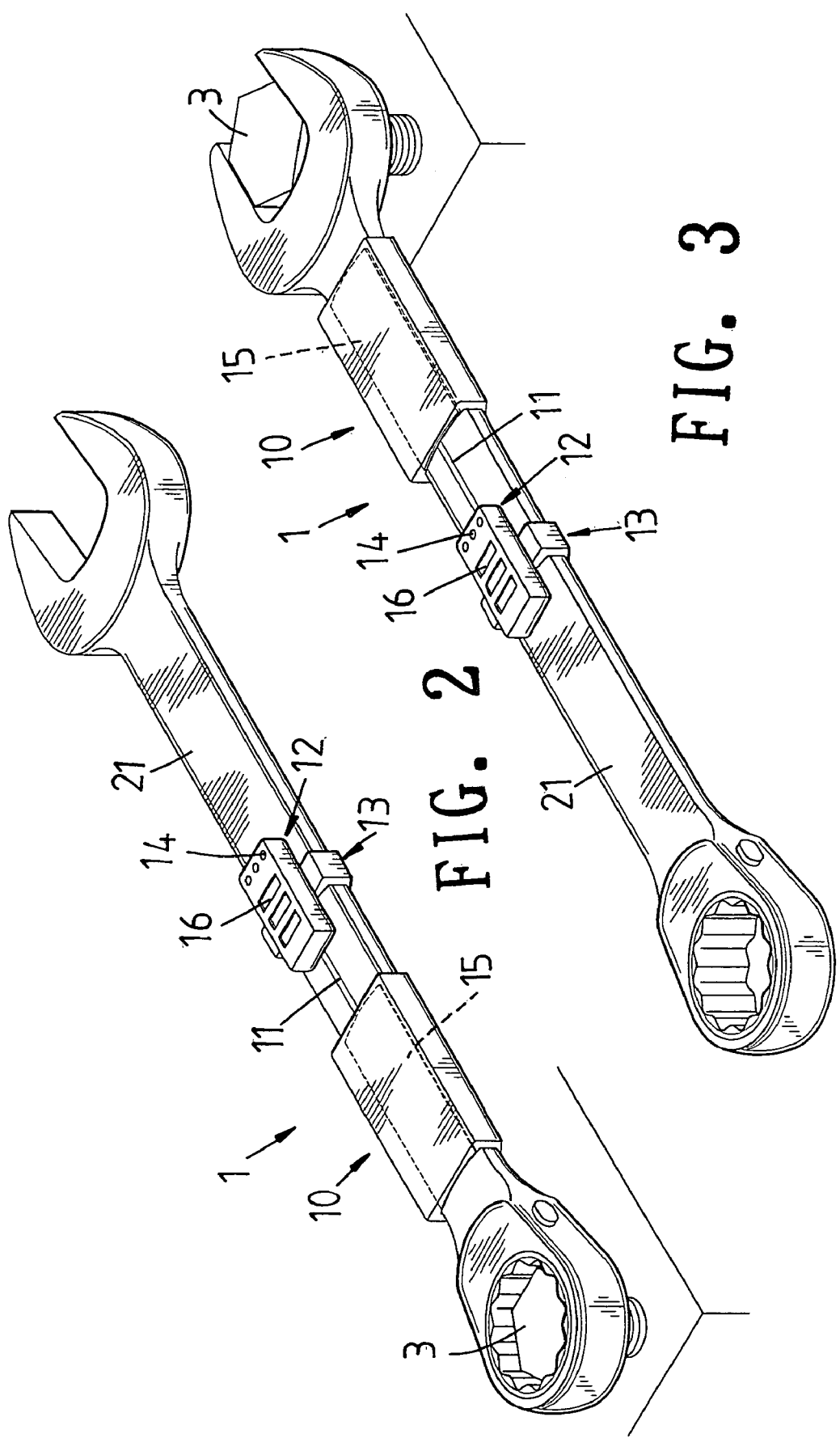

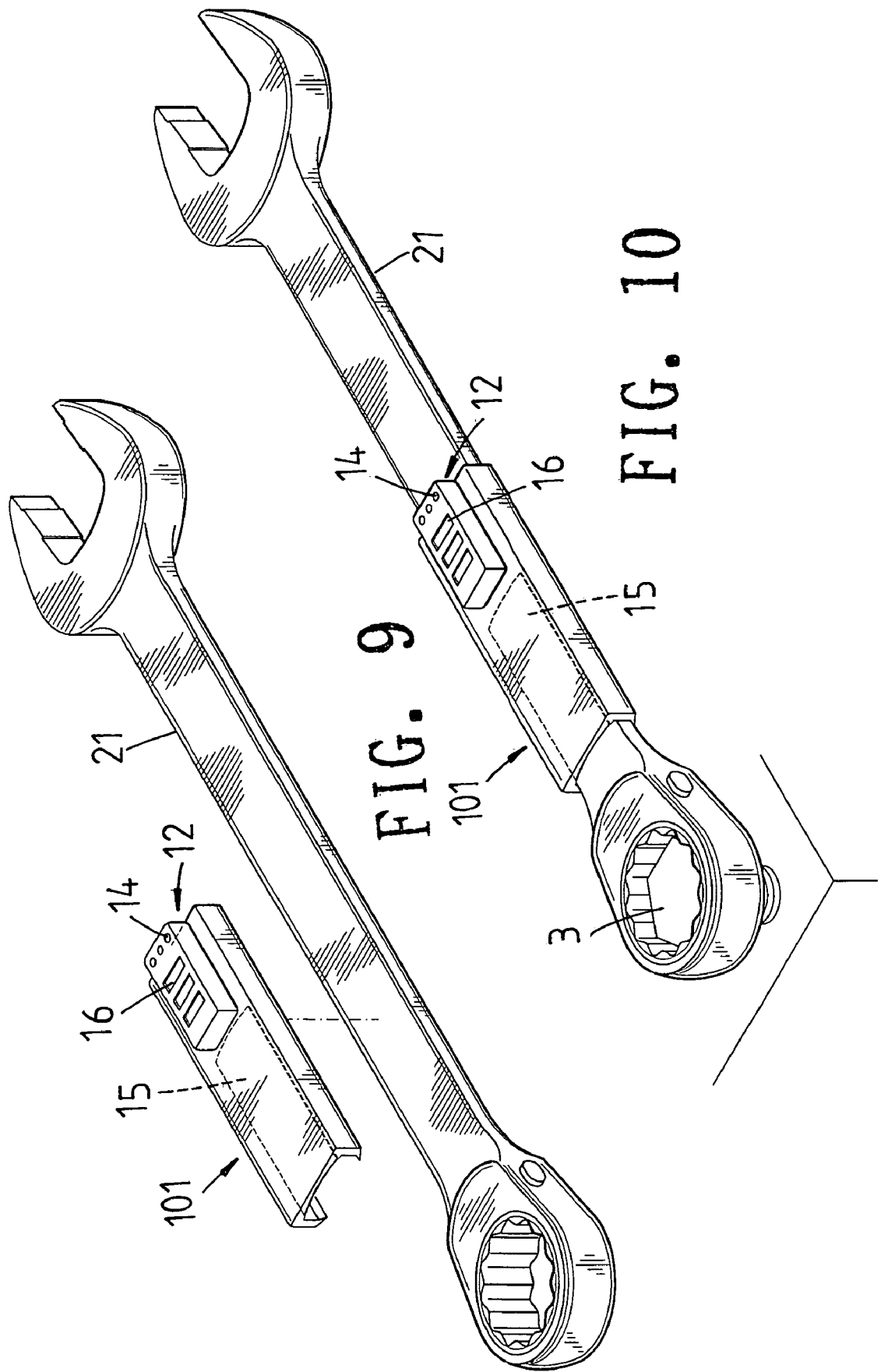

REMOVABLE TWISTING MEASURING DEVICE FOR VARIOUS HAND TOOLS

FIELD OF THE INVENTION

The present invention relates to twisting measuring device, and particularly to a removable twisting measuring device for various hand tools.

BACKGROUND OF THE INVENTION

In one prior art, a sensor is installed in a rod body of a ratchet wrench. The sensor includes a digital display, a strain gauge and a signal amplifier. The deformation of the strain gauge generates a variation of resistance so as to derive the twisting force applied thereon. For this arrangement, the rod body must be formed with a through hole or a groove for installing the sensor. Then the rod body is refinished so that the cost is high.

Moreover, since the strain gauge is installed within the rod body, it is inseparable. Thereby for different hand tool, a different strain gauge is necessary and thus the cost is increased.

SUMMARY OF THE INVENTION

Accordingly, the primary object of the present invention is to provide a twisting measuring device which can be engaged to hand tools. One end of the twisting measuring device is installed with a first cover and another end thereof is installed with a display device. A transfer element is connected between the first cover and the display device.

The first cover is made by aluminum alloy which has a preferred deformation ability. An appearance of the first cover is matchable to the U shape of the rod body of a hand tool. Furthermore, the first cover has a strain gauge. As a force is applied the strain gauge. A resistance variation thereof will be detected and then the variation will be displayed on the display device through the transfer element so as to calculate twisting force. The strain gauge is known in the prior art and thus the details will not be described here.

A display device has a screen at one surface thereof for displaying the twisting force. A calibrating button is installed on the surface for calibrating the resistance sensitivity of the strain gauge so as to match the strength of a measured hand tool.

Furthermore, a lower end of the display device is installed with a U shape second cover so that the display device can be easily engaged to the rod body of the hand tool.

Furthermore, to make the first cover can be engaged to a round rod body of a hand tool. The twisting measuring device is made of aluminum alloy with preferred deforming ability. The first cover has a C-like shape for matching the shape of the hand tool. The display device is pivotally installed to a second cover which also has a C-like shape. The twisting measuring device has the same effect as that in the first embodiment when it is engaged to the rod body.

Furthermore, in the present invention, it is possible that only one cover is formed. An inner surface of the cover is embedded with a strain gauge and another end thereof is installed with a display device. Thereby the same effect can be achieved.

The various objects and advantages of the present invention will be more readily understood from the following detailed description when read in conjunction with the appended drawing.

BRIEF DESCRIPTION OF THE DRAWINGS

FIG. 2 shows one operation of the present invention.

FIG. 3 shows another operation of the present invention.

FIG. 9 is a schematic view of the third embodiment of the present invention before installation.

FIG. 10 shows the operation of the third embodiment of the present invention.

DETAILED DESCRIPTION OF THE INVENTION

In order that those skilled in the art can further understand the present invention, a description will be described in the following in details. However, these descriptions and the appended drawings are only used to cause those skilled in the art to understand the objects, features, and characteristics of the present invention, but not to be used to confine the scope and spirit of the present invention defined in the appended claims.

Figure 1:
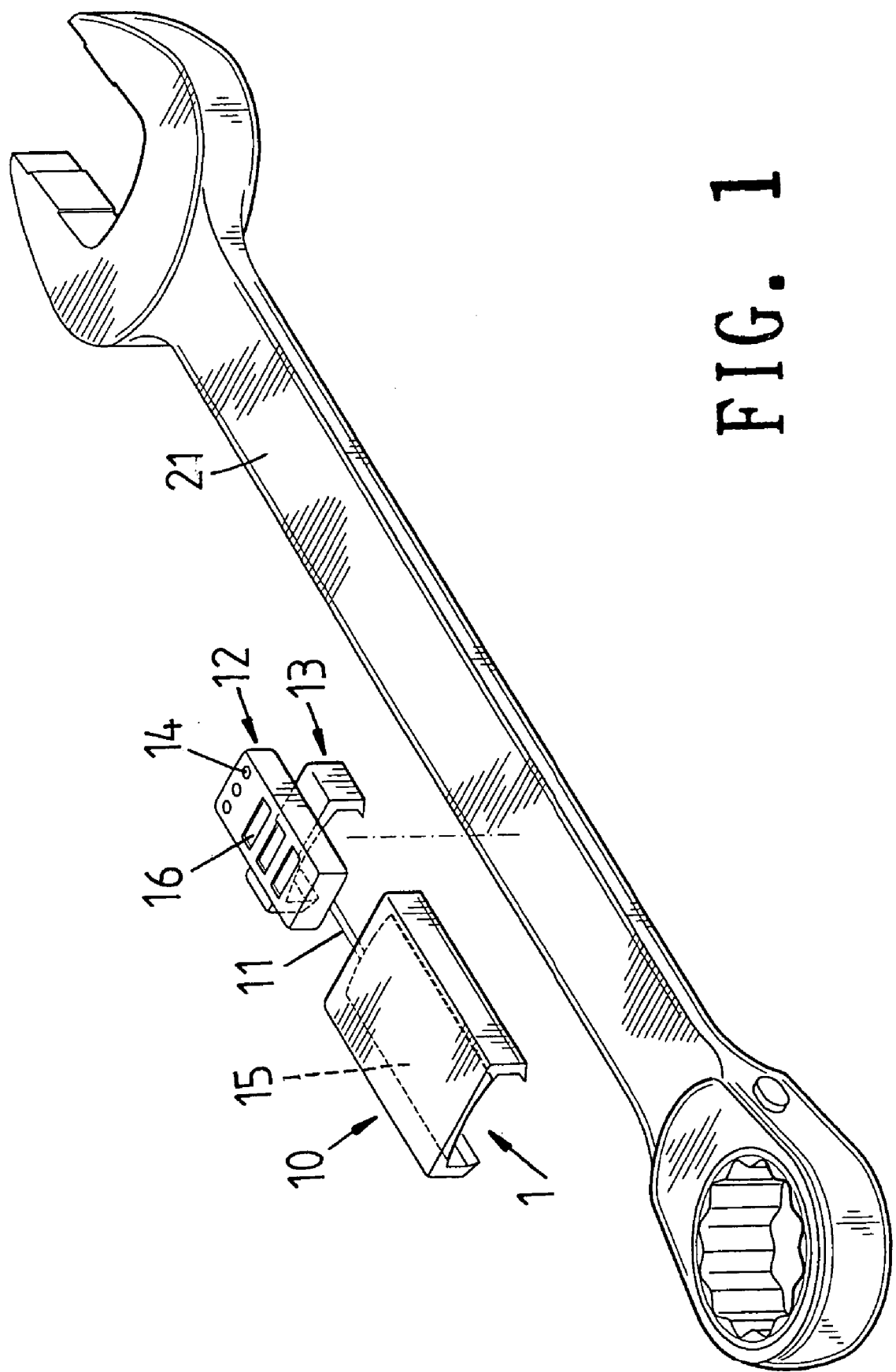
FIG. 1 is a schematic view of the twisting measuring device for various hand tools before installation.

Referring to FIG. 1, the twisting measuring device for various hand tools of the present invention is illustrated. The twisting measuring device has the following elements.

A twisting measuring device 1 can be engaged to one hand tool. One end of the twisting measuring device 1 is installed with a first cover 10 and another end thereof is installed with a display device 12. A transfer element 11 is connected between the first cover 10 and the display device 12.

In this embodiment, the first cover 10 is made by aluminum alloy which has a preferred deformation ability. An appearance of the first cover 10 is matchable to the U shape of the rod body 21 of a hand tool. Furthermore, the first cover 10 has a strain gauge 15. As a force is applied the strain gauge 15. A resistance variation thereof will be detected and then the variation will be displayed on the display device 12 through the transfer element 11 so as to calculate twisting force. The strain gauge is known in the prior art and thus the details will not be described here.

A display device 12 has a screen 16 at one surface thereof for displaying the twisting force. A calibrating button 14 is installed on the surface for calibrating the resistance sensitivity of the strain gauge 15 so as to match the strength of a measured hand tool.

Furthermore, a lower end of the display device 12 is installed with a U shape second cover 13 so that the display device 12 can be easily engaged to the rod body 21 of the hand tool.

Figure 4:
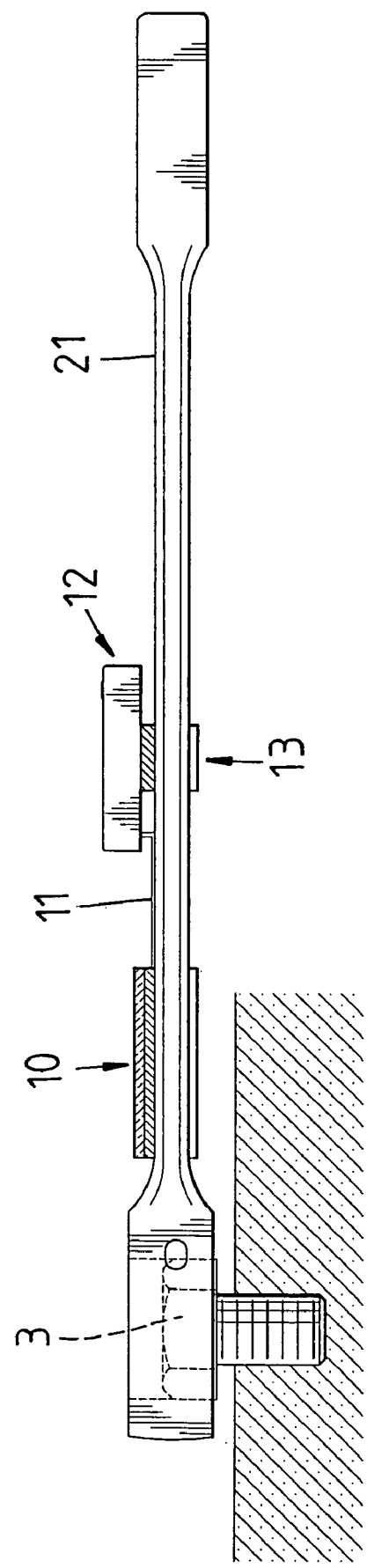
FIG. 4 is a lateral view about the operation of the present invention.

In use of the present invention, as shown in FIGS. 2 and 4, the first cover 10 and second cover 13 are engaged to the rod body 21 of the hand tool. The calibrating button 14 on the display device 12 is calibrated in advance for matching the structure and strength of the hand tool so as to have an optimum resistance sensitivity. When the hand tool, for example, a spanner, is used, the rod body 21 of the hand tool deforms due to a force applied thereon. The strain gauge 15 in the first cover 10 engaged to the rod body 21 of the hand tool also deforms. The deformation of the strain gauge will be transferred to the display device 12 through the transfer element 11 so as to get a corresponding resistance variation and then a twisting force is derived and is displayed on the screen 16. Thereby the user may know whether an object is tightened.

Figure 5:
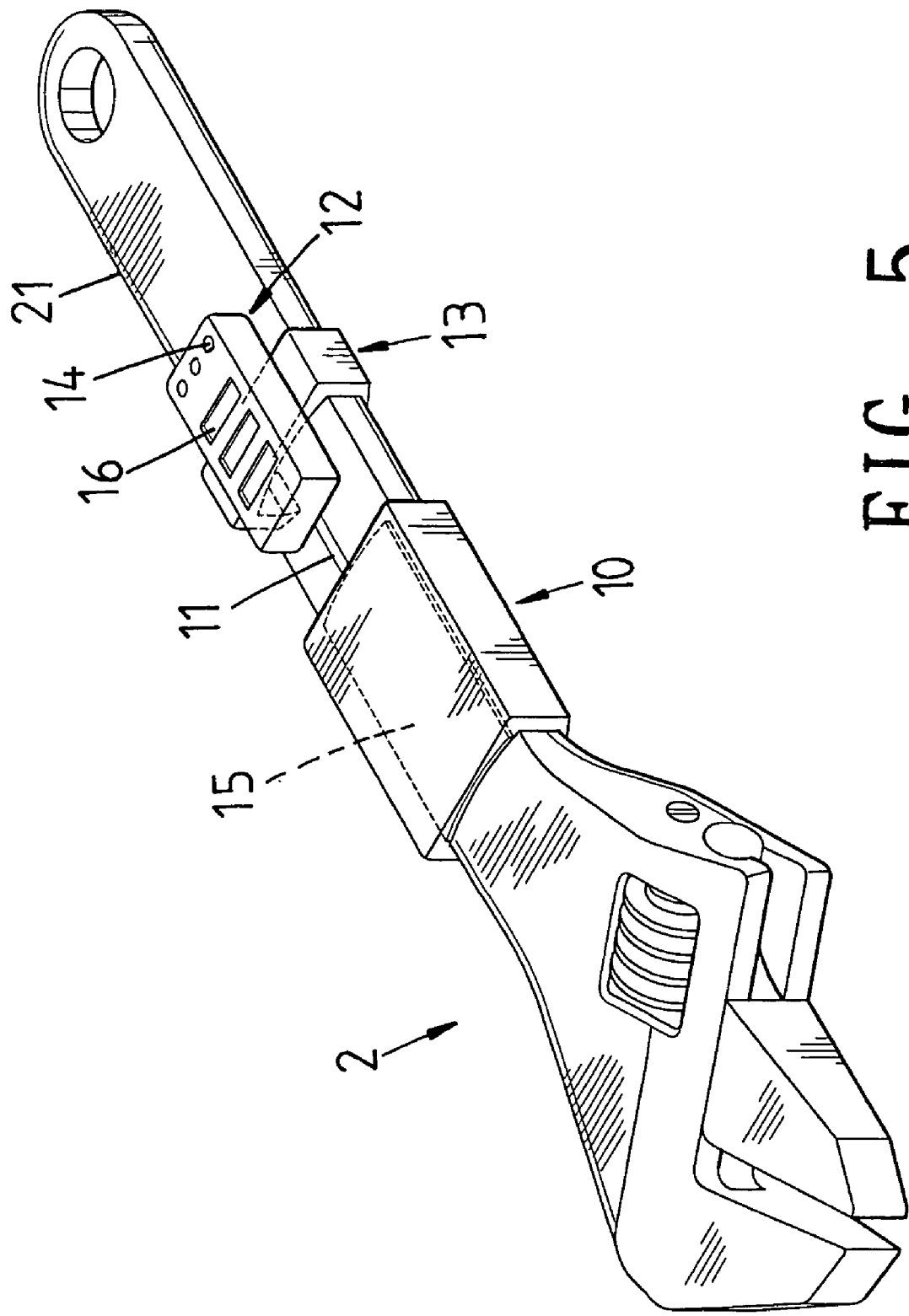
FIG. 5 is a schematic view of the twisting measuring device for various hand tools of the present invention, where the present invention has been installed.

Furthermore, referring to FIG. 5, when the twisting measuring device for various hand tools of the present invention is engaged to a rod body 21 of a movable spanner 2. The present invention can be used to measure the twisting force of the movable spanner 2 without using a new movable spanner building with a twisting measuring device therein. Thus the cost is saved.

Figure 6:
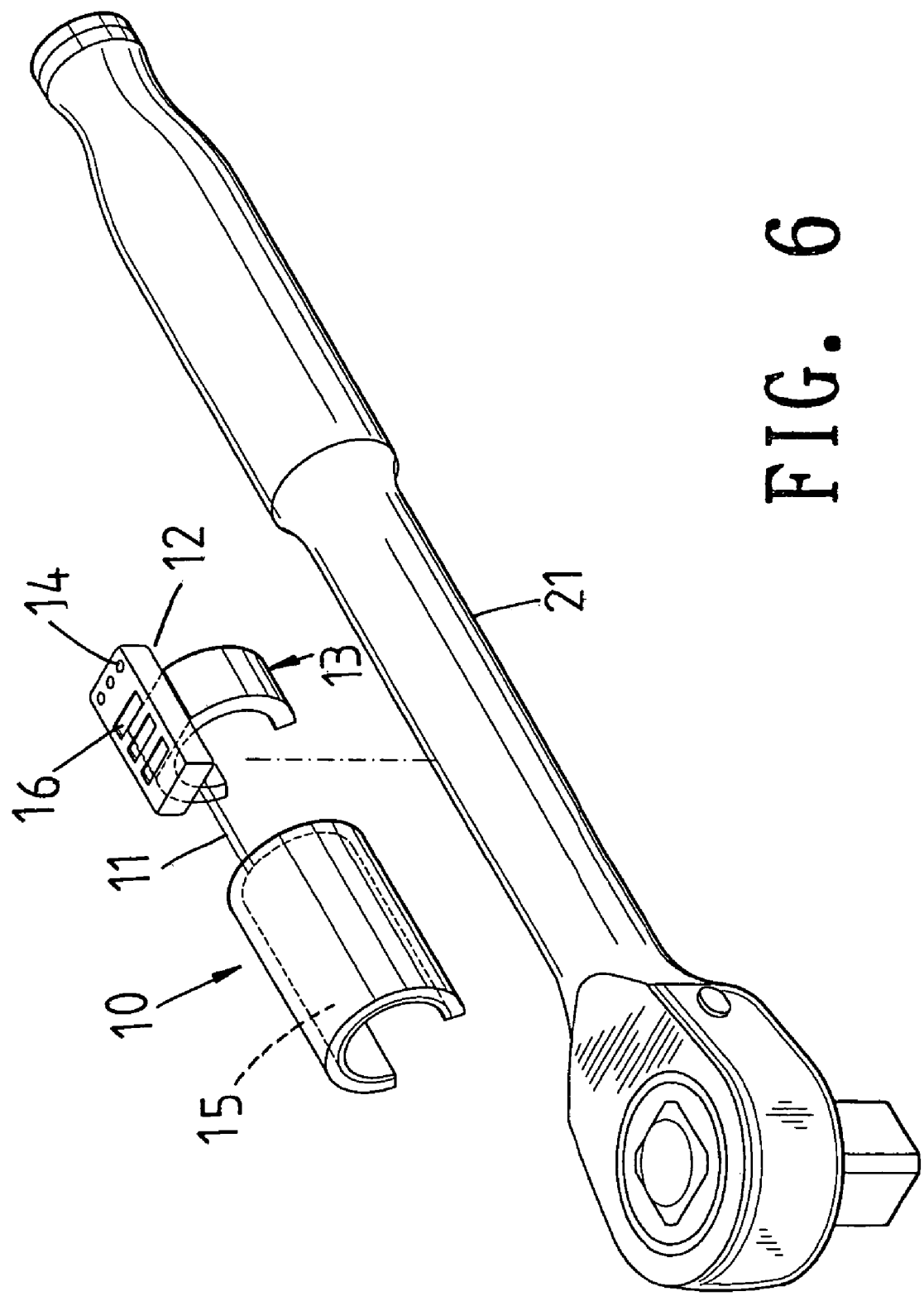
FIG. 6 is a schematic view of the second embodiment of the present invention before installation.
Figure 7:
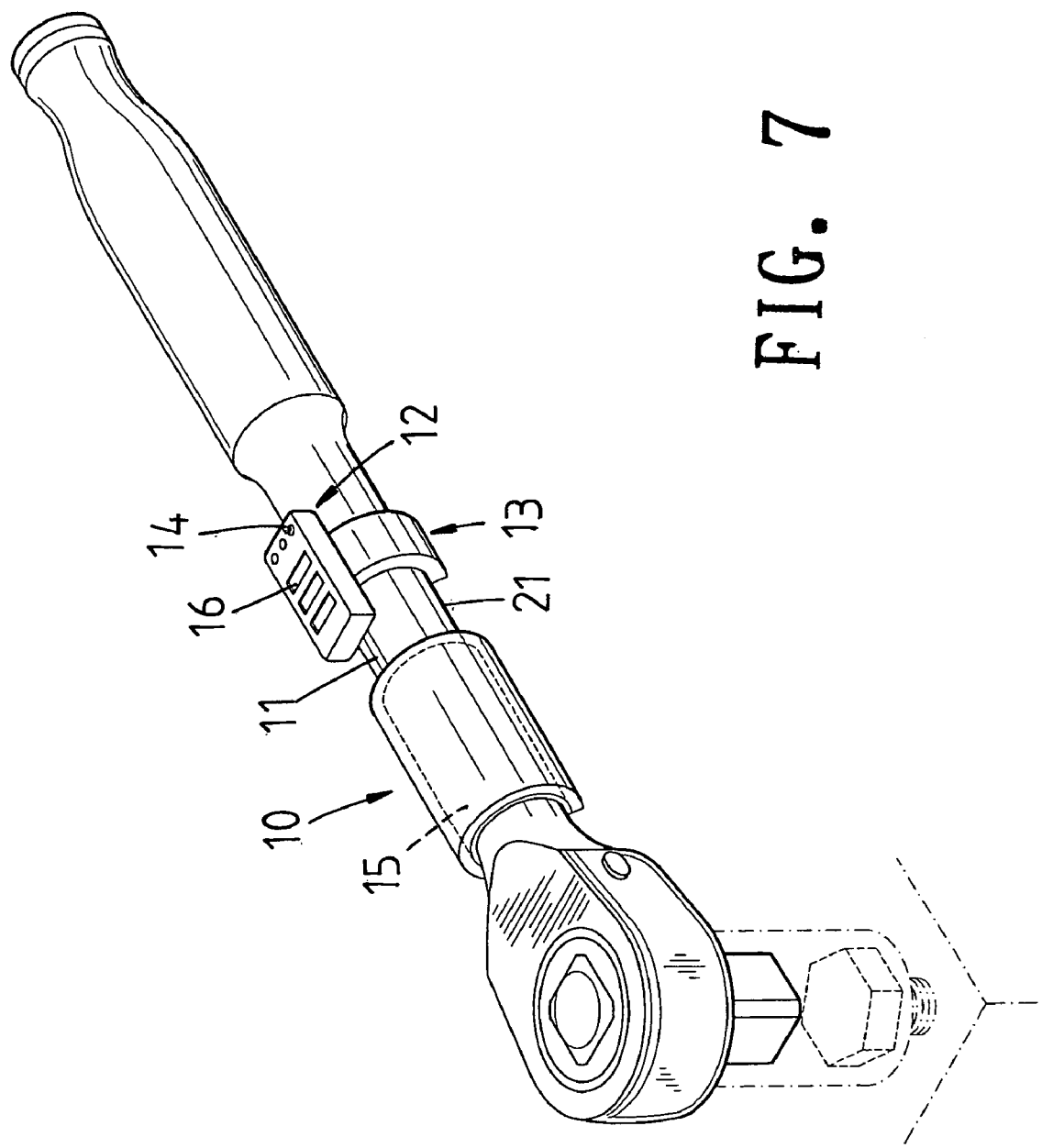
FIG. 7 shows the operation of the second embodiment of the present invention.
Figure 8:
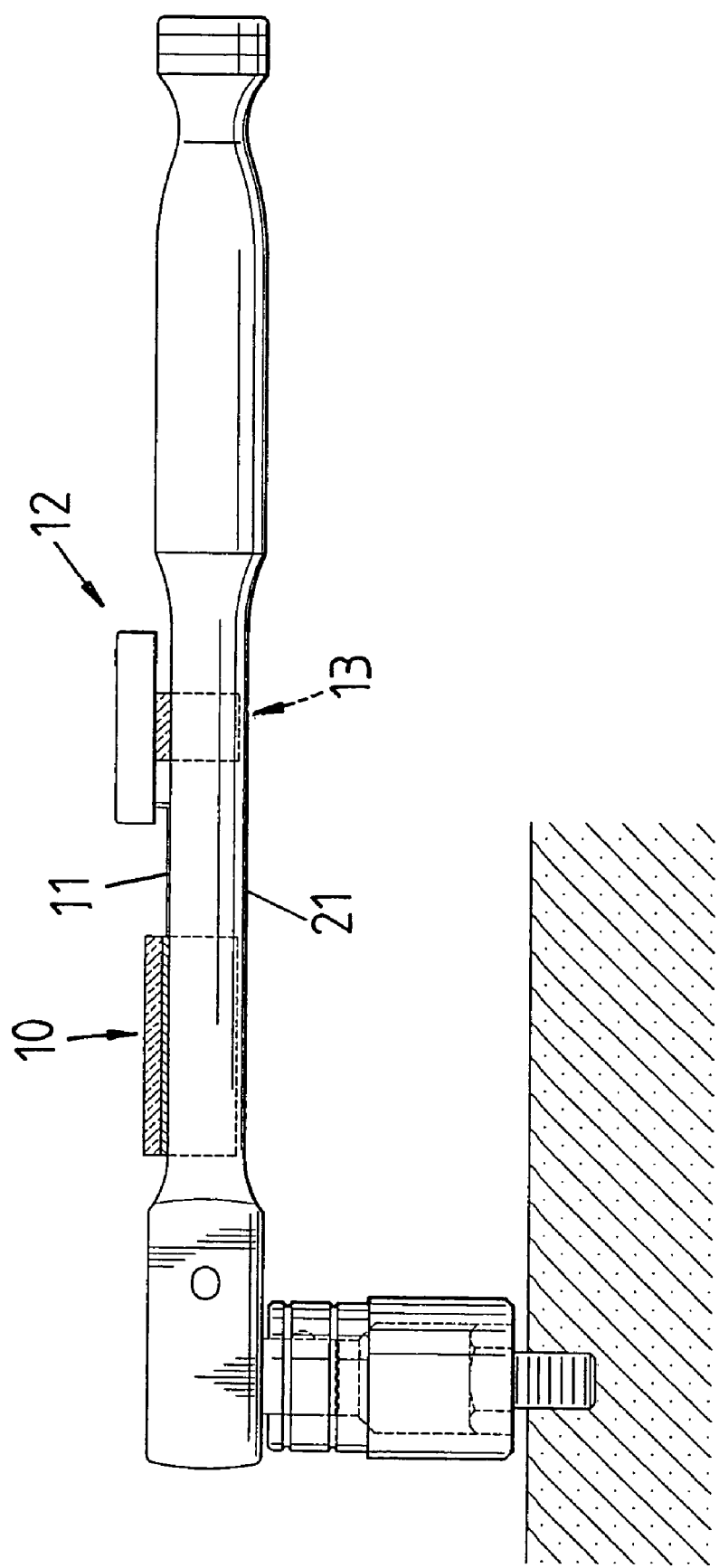
FIG. 8 is a lateral view about the operation of the present invention.

With reference to FIGS. 6 to 8, the second embodiment of the present invention is illustrated. In this the present invention, the structure and functions of the transfer element 11 and the display device 12 are identical to those in the first embodiment. Thus the details of these two elements will not be further described here. Only the differences of these two embodiments will be described hereinafter. To make the first cover 10 can be engaged to a round rod body 21 of a hand tool. The twisting measuring device is made of aluminum alloy with preferred deforming ability. The first cover 10 has a C-like shape for matching the shape of the hand tool. The display device 12 is pivotally installed to a second cover 13 which also has a C-like shape. The twisting measuring device has the same effect as that in the first embodiment when it is engaged to the rod body 21.

Figure 11:
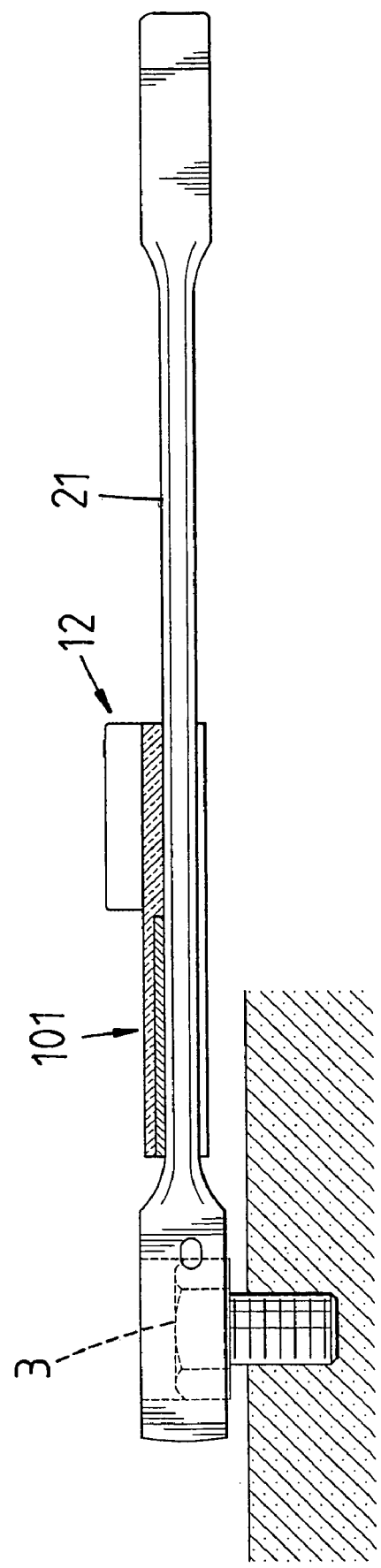
FIG. 11 is a lateral view of the operation of the third embodiment of the present invention.

With reference to FIG. 9 to 11, the third embodiment of the twisting measuring device for various hand tools of the present invention is illustrated. The object of this embodiment is to cause the work of assembling the twisting measuring device to be performed easily and quickly and to prevent the strain gauge 15 in the first cover 10 and the transfer element 11 of the display device 12 on the second cover 13 from breaking. Thereby only one cover 101 is formed. An inner surface of the cover 101 is embedded with a strain gauge 15 and another end thereof is installed with a display device 12. Thereby the same effect can be achieved.

Figure 12:
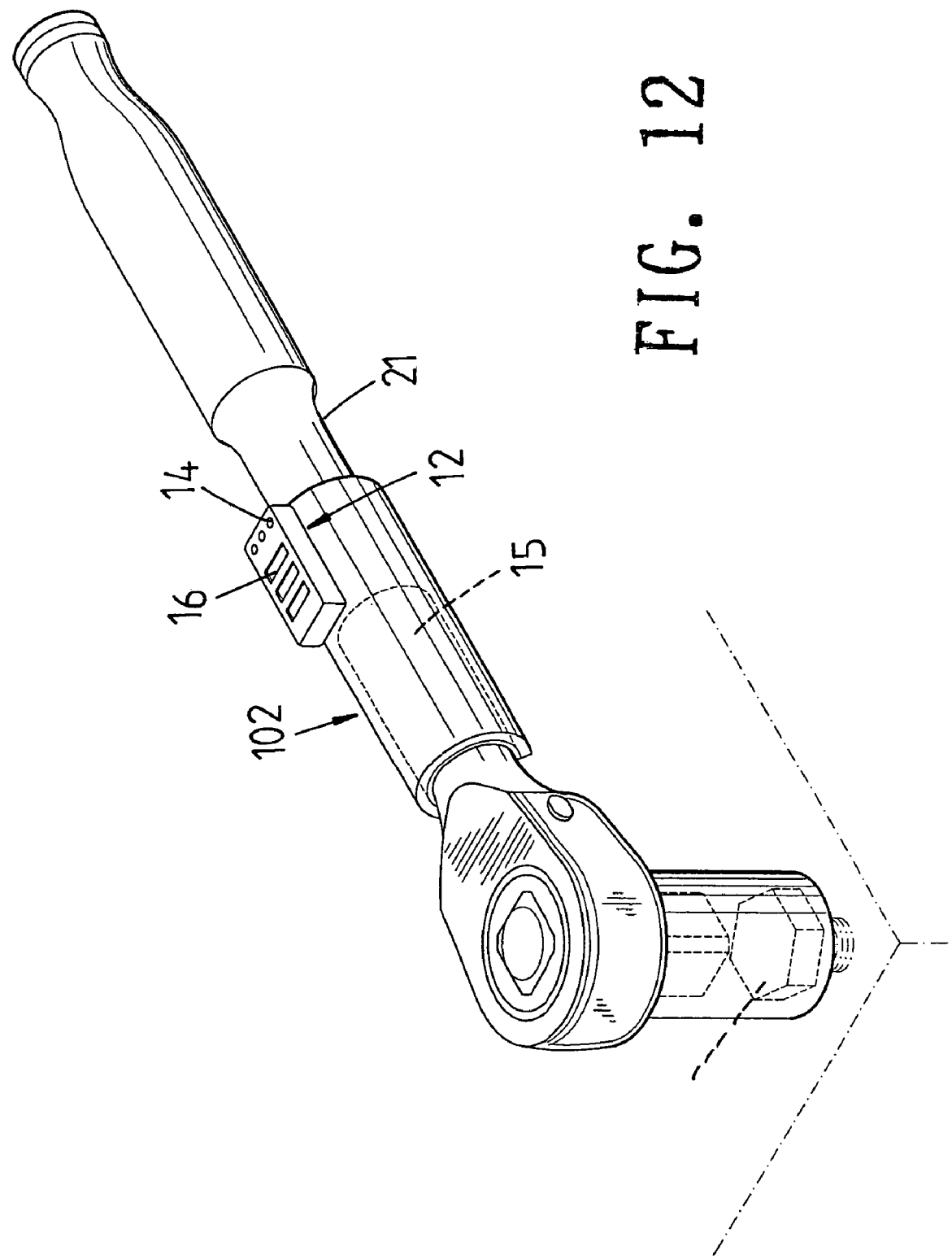
FIG. 12 is a structural schematic view of the third embodiment according to the present invention.

However in the present invention, the first cover 10, second cover 13 and cover 101 can be made by other material, such as plastics, or others with having preferred deformity. Thereby as shown in FIG. 12, the cover 101 may have a C-like shape.

The present invention is thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A removable twisting measuring device for various hand tools comprising:
   a first cover removably installed on a rod body of a hand tool;
   a strain gauge installed at one end of the first cover contacting the rod body of the hand tool; the strain gauge having a deformation as a twisting force is applied thereon;
   a second cover removably installed on the rod body of the hand tool;
   a display device installed on the second cover; the display device having a transfer element; resistance variation due to the deformation of the strain gauge being transferred to the display device so as to derive the twisting force which is then displayed on the display device.

2. The removable twisting measuring device for various hand tools as claimed in 1, wherein the cover is made from one of aluminum alloys and deformable materials.

3. The removable twisting measuring device for various hand tools as claimed in 1, wherein the display device has a screen and a calibrating button.

* * * * *